United States Patent [19]
Bucholtz et al.

[11] Patent Number: 5,739,536
[45] Date of Patent: Apr. 14, 1998

[54] FIBER OPTIC INFRARED CONE PENETROMETER SYSTEM

[75] Inventors: Frank Bucholtz, Crofton, Md.; Gregory Nau, Alexandria; Ishwar D. Aggarwal, Fairfax Station, both of Va.; Jasbinder S. Sanghera, Greenbelt; Kenneth J. Ewing, Bowie, both of Md.

[73] Assignee: The United States of America as represented by the Secretary of the Navy, Washington, D.C.

[21] Appl. No.: 572,389

[22] Filed: Dec. 14, 1995

[51] Int. Cl.⁶ .......................... G01J 5/02
[52] U.S. Cl. ................ 250/341.2; 250/339.11; 250/253; 250/339.12
[58] Field of Search .............. 250/341.2, 339.11, 250/339.1, 339.12, 341.8, 253

[56] References Cited

U.S. PATENT DOCUMENTS

| | | | |
|---|---|---|---|
| 4,266,878 | 5/1981 | Auer | 250/339.11 |
| 4,390,514 | 6/1983 | Chianelli et al. | 423/509 |
| 4,612,294 | 9/1986 | Katsuyama et al. | |
| 4,766,315 | 8/1988 | Hellstrom et al. | 250/339.1 |
| 4,942,144 | 7/1990 | Martin | 501/40 |
| 5,010,776 | 4/1991 | Lucero et al. | 73/863.23 |
| 5,038,040 | 8/1991 | Funk et al. | 250/339.11 |
| 5,097,129 | 3/1992 | de Vries et al. | 250/341.8 |
| 5,128,882 | 7/1992 | Cooper et al. | 364/550 |
| 5,157,457 | 10/1992 | Taylor | 250/227.19 |
| 5,246,862 | 9/1993 | Grey et al. | 436/28 |
| 5,316,950 | 5/1994 | Apitz et al. | 436/28 |
| 5,445,795 | 8/1995 | Lancaster et al. | 422/86 |
| 5,461,229 | 10/1995 | Sauter et al. | 250/253 |

FOREIGN PATENT DOCUMENTS 8302326  7/1983  WIPO .......... 250/341.8

OTHER PUBLICATIONS

Publication, "Fiber Optic IR Reflectance Sensor for the Cone Penetrometer" by G. Nau et al., SPIE Germany 1995, Jun., SPIE vol. 2504, pp. 291–296 (1995).

Publication, "Fiber–Optic Near–Infrared Reflectance Sensor For Detection of Organics in Soils", by Irwin Schneider et al., IEEE Photonics Technology Letters, vol. 7, No. 1 (Jan. 1995).

Publication, "Fiber Optic Infrared Reflectance Probe for Detection of Hydrocarbon Fuels in Soil" by K.J. Ewing et al., SPIE, vol 2367, McLean, VA, 9–10 No. 94, pp. 17–23 (1995). no month.

Publication, "Fabrication of Low–Loss Ir–Transmitting $Ge_{30}As_{10}Se_{30}Te_{30}$ Glass Fibers" by J. S. Sanghera et al., Journal of Lightwave Technology, vol. 12, No. 5 pp. 737–741, (May 1994).

(List continued on next page.)

*Primary Examiner*—Don Wong
*Attorney, Agent, or Firm*—Thomas E. McDonnell; George Jameson

[57] ABSTRACT

A system for the in-situ detection of chemicals, including water, in soil comprises: a penetrometer for penetrating the soil, the penetrometer including interior and exterior surfaces, and a window for allowing infrared radiation to be transmitted between the interior and exterior surfaces of the penetrometer; a driver for driving the penetrometer into the soil to a plurality of different depths; a source for providing infrared radiation which passes through the window to irradiate the soil adjacent to the window; an infrared transmitting chalcogenide optical fiber; an optical system disposed within the penetrometer adjacent to the window for transmitting infrared radiation from the source through the window into the soil and for collecting infrared radiation reflected from the soil back through the window into a first end of the chalcogenide fiber; and a spectrometer coupled to a second end of the infrared transmitting chalcogenide optical fiber for receiving and analyzing the reflected infrared radiation passing through the chalcogenide optical fiber to obtain information on chemicals present at various depths of the soil through which the penetrometer passes.

27 Claims, 7 Drawing Sheets

OTHER PUBLICATIONS

Publication, entitled "Optical and Mechanical Properties of IR Transmitting Chalcogenide Glass Fibers" by S. Sanghera et al. in Optical Network Engineering and Integrity, published by SPIE, vol. 2611, pp. 2–6, (24–25 Oct. 1995).

Publication, "Fabrication of Long Lengths of Low–Loss IR Transmitting $As_{40}S$ $(60-_x)Se_x$ Glass Fibers" by J.S. Sanghera et al., Journal of Lightwave Technology, vol. 14, No. 5, pp. 743–749 (May 1996).

IR SOURCE IN
ELLISOIDAL OR
PARABOLOIDAL
REFLECTOR

IR SOURCE IN
SPHERICAL
REFLECTING CAVITY

IR SOURCE IN
ELLISOIDAL
REFLECTING CAVITY

PARABOLOIDAL
MIRROR

ELLIPSOIDAL
MIRROR

FLAT MIRROR

LIGHT REFLECTING
ON SOIL SURFACE

COLLIMATING
OR FOCUSING
LENS

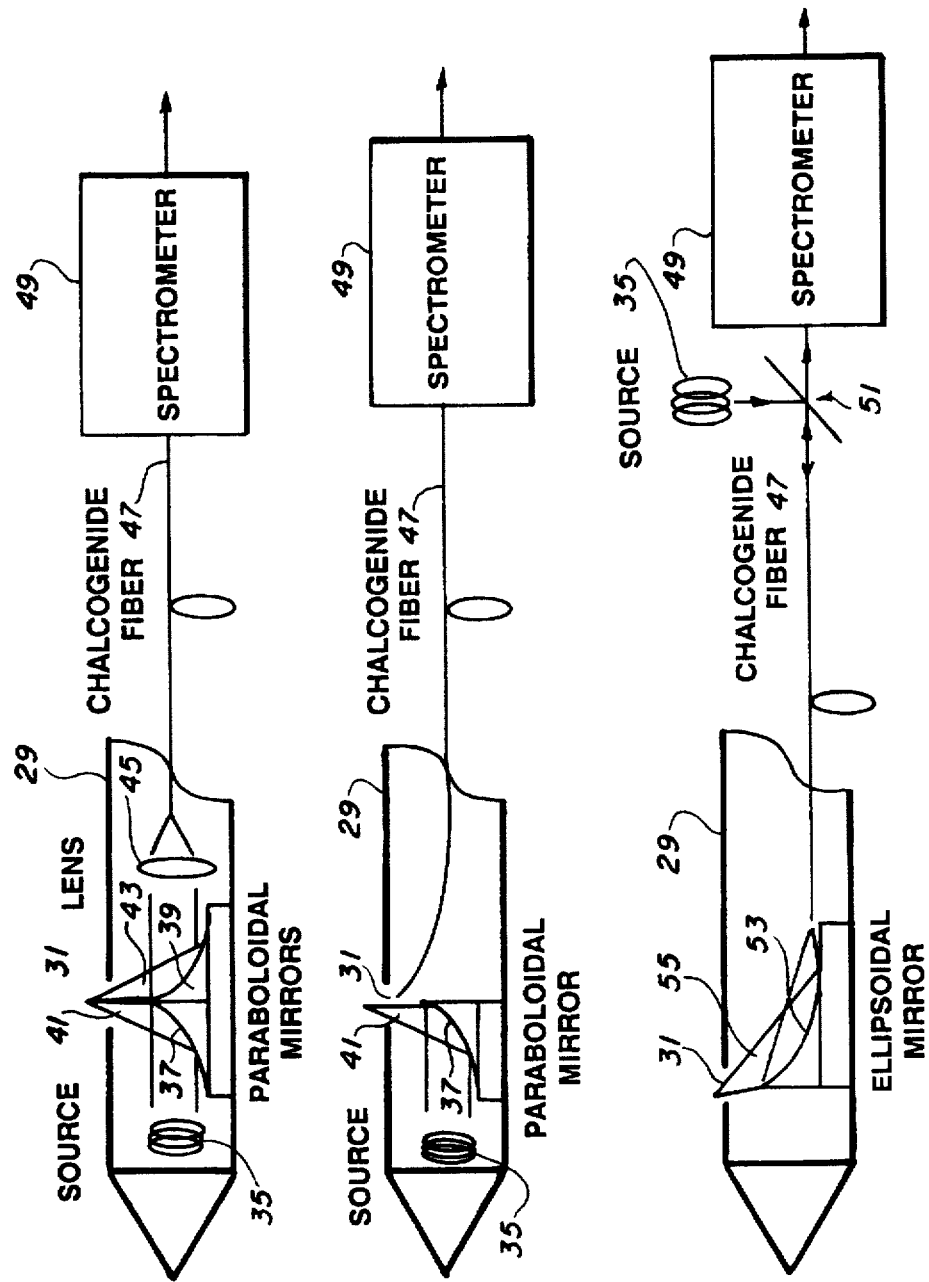

2

FIBER OPTIC INFRARED CONE PENETROMETER SYSTEM

BACKGROUND OF THE INVENTION

1. Field of the Invention

The present invention relates to the detection and analysis of chemicals (including water) in soil and particularly to a system for performing remote, in-situ infrared (IR) spectroscopy of soils and soil-liquid mixtures in the 2 to 12 micron wavelength range.

2. Description of Related Art

In many places throughout the world there are industrial and governmental sites that are suspected of being contaminated with various chemical wastes. An extensive effort is presently underway to characterize, monitor and clean these sites. The first part of this process, the characterization of the waste site, traditionally involves drilling wells and removing core or liquid samples for analysis above ground or even off site. Such characterization methods are expensive and time consuming and involve considerable sampling problems, especially in the case of volatile organic contaminants such as benzene, trichloroethelyne and toluene. To help overcome these problems, the cone penetrometer system has been developed for putting sensors directly into soils.

Cone penetrometry is a well-established technique for the measurement of a variety of subsurface soil parameters. A cone penetrometer consists of a hollow steel tube containing sensing and measurement instruments. The tube is pushed into the soil using a hydraulic ram mounted in a truck and measurements are made at various depths to a maximum depth of approximately 150 feet. With this system, a number of "pushes" can be made rapidly at various locations.

For identification of various chemicals, the penetrometer is typically used to extract samples of soil which are then removed and transported to a laboratory for analysis using, for example, gas chromatography or mass spectroscopy. This process is time and labor intensive and is subject to errors, especially when volatile contaminants are involved. Hence, an in-situ sensor system for detecting, identifying, and quantifying chemicals is needed. One system developed to address this problem is the fiber optic laser-induced flourescence (LIF) system for the cone penetrometer. Here, light from a visible or near-UV laser source is transmitted to the cone penetrometer by a silica optical fiber where it exits the penetrometer tube through a sapphire window and excites the adjacent soil. When excited by near-UV light, certain classes of chemical compounds such as petroleums, oils, and lubricants fluoresce emitting broad spectrum light and, thus, indicate their presence. However, it is difficult to identify specific contaminants and to make quantitative estimates of specific contaminant levels using LIF.

A more suitable technique for identification and quantitative estimation of particular contaminants is infrared spectroscopy. Nearly all chemical contaminants of interest have unique infrared spectra allowing identification of particular species even in the presence of interfering spectra due to additional species. Until recently, it was not possible to perform in-situ IR spectroscopy with the cone penetrometer in the 2 to 12 micron wavelength range because optical fibers with sufficiently low transmission losses in this wavelength range were not available.

SUMMARY OF THE INVENTION

It is therefore an object of the invention to provide a system for performing remote, in-situ infrared (IR) spectroscopy of soils and soil-liquid mixtures in the 2 to 12 micron wavelength range.

Another object of the invention is to provide a fiber optic infrared spectroscopic system for use with a cone penetrometer to identify and quantify organic contaminants in soil.

Another object of the invention is to transmit optical radiation in the 2-12 micron wavelength range via an infrared-transmitting optic fiber to an optical system in a cone penetrometer tube.

Another object of the invention is to provide an optical system for the efficient and reproducible transmission of infrared light to a region of the soil surrounding a cone penetrometer tube.

Another object of the invention is to provide an optical system for the efficient collection of infrared light after it has been diffusely-scattered by the soil surrounding a cone penetrometer tube.

Another object of the invention is to provide a means for efficiently coupling light from the output of an infrared transmitting optic fiber into an optical signal processor, such as an infrared spectrometer.

A further object of the invention is to perform remote spectroscopy in the infrared wavelength range using infrared transmitting optical fibers which are based on chalcogenide materials and specially designed transmission/collection optics in order to transmit infrared light out of a window of a cone penetrometer tube into soil around the window, recover some of the scattered light from the soil by way of the window and the transmission/collection optics, inject the recovered scattered light into the infrared transmitting fiber and send it up to the surface for detection and processing.

In a preferred embodiment of the invention, a system for the in-situ detection of organic contaminants in soil comprises: a penetrometer for penetrating the soil, the penetrometer including interior and exterior surfaces, and a window for allowing infrared radiation to be transmitted between the interior and exterior surfaces of the penetrometer; a driver for driving the penetrometer into the soil to a plurality of different depths; a source for providing infrared radiation which passes through the window to irradiate the soil adjacent to the window; an infrared transmitting chalcogenide fiber; an optical system disposed within the penetrometer adjacent to the window for transmitting infrared radiation from the source through the window into the soil and for collecting infrared radiation reflected from the soil back through the window into a first end of the chalcogenide fiber; and a spectrometer coupled to a second end of the infrared transmitting chalcogenide fiber for receiving and analyzing the reflected infrared radiation passing through the chalcogenide fiber to obtain information on contaminants present at various depths of the soil through which the penetrometer passes.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views and wherein:

FIGS. 3A, 3B and 3C illustrate exemplary configurations of some of the components shown in FIGS. 2A through 2H for use in the fiber optic infrared cone penetrometer system of the invention;

DETAILED DESCRIPTION OF THE PREFERRED EMBODIMENTS

Figure 1:
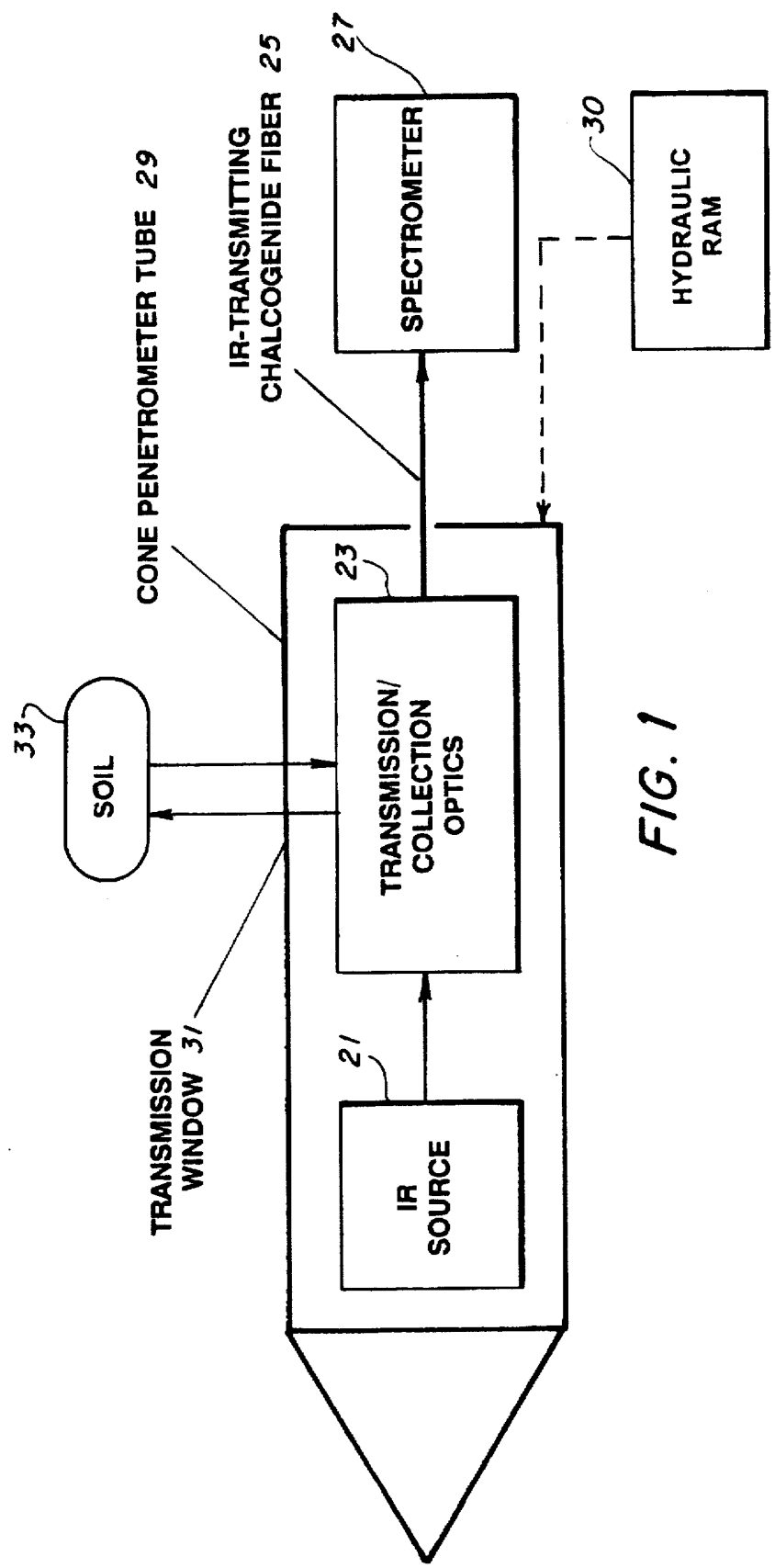
FIG. 1 illustrates a schematic block diagram of the fiber optic infrared cone penetrometer system of the invention.

Referring now to the drawings, FIG. 1 illustrates an exemplary schematic block diagram of a first embodiment of the fiber optic infrared cone penetrometer system of the invention. As shown in FIG. 1, the system of the invention comprises an infrared (IR) source of radiation 21; an optical assembly, comprised of transmission/collection optics 23, which operates over the 2 to 12 micron wavelength range for transmitting light from the IR source 21 to soil 33 and for collecting IR light reflected by the soil 33; an infrared- or IR-transmitting chalcogenide glass optical fiber 25 for transmitting the reflected light recovered from the soil 33 to a remote location above ground; and a remote signal processor, such as a spectrometer 27 above ground which spectrometer 27 includes an optical detector, for analyzing the optical signal transmitted by the optical fiber 25.

Source of IR Radiation

The IR source 21 can be chosen to produce a wideband or narrowband wavelength range within a 2 to 12 micron wavelength range.

Sources for broadband radiation in the infrared are quite simple. A source may be formed, for example, by passing electrical current through a nichrome wire or a glowbar material. Depending on the electrical power and the surface area of the material, sources of this type act effectively as blackbody radiators at effective temperatures in the 300 degree K.–1200 degree K. range. A nichrome wire source operating at approximately 10 Watts and 1000 degrees K. temperature was used for the demonstration system described in FIG. 1. Typically, the source is enclosed in a spherical chamber with highly-reflecting walls and having a small exit aperture. It is also possible to use enclosures having paraboloidal or ellipsoidal shapes.

A second possible source is the tunable IR laser based on quasi-phase matched materials. A device of this type has demonstrated acceptable output power with emission wavelength tunable over the range of 3 to 4 microns.

Transmission/Collection Optics

The purpose of the transmission/collection optics 23 is twofold. First, infrared radiation from the IR source 21 must be directed out through a sapphire transmission window 31 in a penetrometer tube 29 to soil 33. In interacting with the soil 33, the radiation is scattered in effectively all directions due to multiple reflections by soil particles. Some of the scattered radiation must be collected and injected into the optical fiber for transmission to a spectrometer 27. There are many possible arrangements of lenses and various shaped mirrors to efficiently accomplish this dual task of illuminating the soil 33 and collecting the scattered radiation (to be discussed).

IR-Transmitting Chalcogenide Optical Glass Fiber

The optical fiber transmits infrared light from a location underground in the soil to a spectrometer on the surface. To be useful for performing infrared spectroscopy, the fiber must have sufficiently low attenuation in the wavelength range of 2 to 12 microns. Recently, fibers have been fabricated at the Naval Research Lab (NRL) in Washington, D.C., which demonstrate attenuation on the order of 0.2 to 1 dB per meter in this wavelength region (excluding certain known, narrow absorption bands due to impurities.) The glasses manufactured at NRL are based on chalocogenide materials having chemical compositions $As_2S_3$, $As_2Se_3$ and $As_2Te_3$. Optical fibers made with these materials have been manufactured in greater than 50 meter lengths. Other possible fiber materials include fluoride-based glasses and silver-halide-based glasses. However, chalcogenide materials offer the best combination of mechanical and environmental stability and low optical attenuation over a wide range of wavelengths.

The chalcogenide fibers can be produced as either core-only or core-clad type and have an outer Teflon protective jacketing. After fabrication, the fibers can be cabled, if necessary, for use in the field. The inventors at NRL have demonstrated that no degradation in performance is observed for cabled fibers compared to uncabled fibers. Cables can consist of a single fiber or a multiple fiber bundle to increase optical throughput.

An unusual feature of these fibers arises from the high index of refraction ($n \approx 2.4$) of the chalcogenide materials. For core-only fiber, the numerical aperture is approximately 1.0 representing an optical system with extremely high light-gathering capacity. In order to make full use of this high numerical aperture, however, non-imaging optical techniques may need to be employed.

Means for Analyzing the Optical Signal Transmitted by the Optical Chalcogenide Fiber.

After interaction with the soil, the spectral features of the light must be analyzed to gain information on chemical content. Typically this is achieved using an infrared spectrometer. In the demonstration of the system described in this patent application, a commercially available Fourier transform infrared spectrometer was used. The dispersive spectrometer contains a dispersive element, typically a grating, which spreads or disperses the optical signal in space as a function of wavelength. The dispersive spectrometer may be a monochromator, a polychromator, a scanning monochromator, or a spectrograph. The Fourier transform spectrometer consists of an interferometer with some means for producing a periodic, time-varying optical path imbalance and a photodetector. After storing the photodetector output as a function of time, a computer is used to perform a Fourier transform to recover the spectral shape as a function of wavelength (or wavenumber).

The spectrometer analyzes the spectral content of radiation from the soil 33 after it has passed through the optical fiber. By comparing the spectrum (intensity versus wavelength) with the probe in the soil 33 to a reference spectrum taken with the probe outside the soil, information on the chemical content of the soil 33 can be obtained. Most spectrometers for the infrared wavelength fall into one of two catagories: (1) dispersive or (2) Fourier transform. In the dispersive spectrometer, an optical element causes light at different wavelengths to be refracted by slightly different angles. Hence, by measuring the amount of light at each angle, the spectrum can be obtained. In a Fourier transform spectrometer, an interferometer with a time varying optical path difference causes the intensity of light at different wavelengths to oscillate at slightly different frequencies. By recording these oscillations as a function of time and mathematically performing a Fourier transform on the data, the spectrum is obtained.

Returning to the embodiment of FIG. 1, the IR source 21 and the transmission/collection optics 23 are contained in a cone penetrometer tube 29 which is pushed into the ground by, for example, a hydraulic ram 30 mounted in a truck (not shown) and measurements are made at various depths to a maximum depth of approximately 150 feet. The cone penetrometer tube 29 terminates in a cone which tapers to a point, as shown in FIGS. 3A, 3B and 3C, as well as in FIG. 1. The spectrometer 27 is located on or above the ground.

In the operation of FIG. 1, infrared radiation from the IR source 21 is transmitted by way of the transmission/collection optics 23 through a transmission window 31 in the cone penetrometer tube 20 into soil 33 adjacent to the transmission window 31. IR light reflected from the soil 33 passes back through the transmission window 31 and is collected by the transmission/collection optics 23. The infrared optics or transmission/collection optics 23 are specially designed to perform the transmission and collection of IR light. Reflected IR light collected by the transmission/collection optics 23 is injected into the infrared- or IR-transmitting chalcogenide optical fiber 31 for transmission to the above-ground remote spectrometer 33 for analysis of the wavelength(s) and amplitude(s) of the reflected optical signal to determine the type(s) and concentration(s) of various hydrocarbon contaminants in the soil at different depths.

Figure 2A:
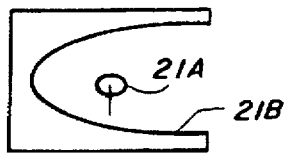
FIGS. 2A, 2B and 2C illustrate three exemplary ways of placing an infrared source in a cavity for subsequent transmission of infrared light to the transmission/collection optics.
Figure 2B:
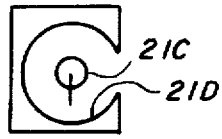
Figure 2C:
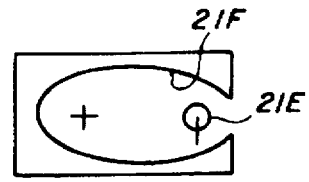

Three exemplary ways of placing a broadband infrared source in a cavity for subsequent transmission of infrared light to the transmission/collection optics 23 are illustrated in FIGS. 2A, 2B and 2C, which will now be discussed.

FIG. 2A illustrates a broadband IR source 21A in either an ellipsoidal or paraboloidal shaped reflector 21B. The IR source 21A is located at the focus of a reflector 21B and the reflector 21B concentrates and reflects the light from the reflector 21B.

FIG. 2B illustrates a broadband IR source 21C in a spherical reflecting cavity 21D.

FIG. 2C illustrates a broadband IR source 21E located at one of the focal points in an ellipsoidal-shaped cavity 21F. In this case some of the light would directly come out from the source 21E while the rest of the light would bounce around in the cavity 21F before it exits the cavity 21F.

Thus, FIGS. 2A, 2B and 2C illustrate three different ways of placing a broadband IR source in a cavity in order to, with a degree of efficiency, transmit IR light toward the transmission/collection optics 23 portion of the fiber optic infrared cone penetrometer system.

Other General Component Descriptions For Reflectance Probe Designs

Other reflective elements that can be used inside the transmission/collection optics 23 of FIG. 1 will be discussed by now referring to FIGS. 2D, 2E and 2F.

Figure 2D:
FIGS. 2D, 2E and 2F illustrate three exemplary types of mirrors that can be selectively utilized in the transmission/collection optics.

FIG. 2D illustrates a paraboloidal mirror in which the reflective surface is in the shape of a portion of a paraboloid.

Figure 2E:
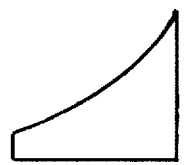

FIG. 2E illustrates an ellipsoidal mirror in which the reflective surface is in the shape of a portion of an ellipsoid. The ellipsoidal mirror has two focal points and possesses the property wherein any light ray which passes through one focal point and is incident on the ellipsoid surface will be reflected on a path which passes through the second focal point. An ellipsoidal mirror can be used either singly or as a pair to transmit to and collect reflected light from the soil in the cone penetrometer. In addition, an ellipsoidal mirror can be used in conjunction with a paraboloidal mirror or with a flat mirror.

Figure 2F:
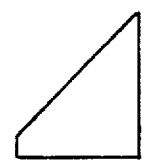

FIG. 2F illustrates a typical flat mirror. The flat mirror offers reduced transmission and collection efficiency, but is much easier to fabricate.

Other Symbols Used For The Purpose Of The Diagrams

Figure 2G:
FIG. 2G illustrates a symbol representative of light reflecting from a soil surface.

FIG. 2G illustrates a rising sun symbol representative of IR light reflecting from the surface of the soil 33 just outside of the transmission window 31 of the cone penetrometer tube 29.

Figure 2H:
FIG. 2H illustrates a collimating or focusing lens.

FIG. 2H illustrates a collimating or focusing lens.

It should be noted at this time that different combinations of the optical components illustrated in FIGS. 2A through 2H can be used to transmit light by way of the transmission/collection optics 23 out of the transmission window 31 of the cone penetrometer 29 into the soil 33, to recover or collect the light that is reflected by the soil 33 back though the transmission window 31 and the transmission/collection optics 23, and to inject that reflected light into the IR transmitting chalcogenide fiber 25.

FIGS. 3A, 3B and 3C illustrate three different combinations of the optical components of FIGS. 2A through 2H for forming exemplary configurations of the fiber optic infrared cone penetrometer.

FIG. 3A shows a standard configuration, where the IR source 35 (of FIG. 2A) is located in the penetrometer tube 29 and two back-to-back paraboloidal mirrors 37 and 39 (see FIG. 2D) are utilized as the transmission/collection optics 23. Paraboloidal mirror 37 is used to reflect IR light 41 from the source 35 through the transmission window 31 into the soil 33. Paraboloidal mirror 39 directs IR light 43 that is reflected from the soil 33 and through the transmission window 31 toward a focusing lens 45 (see FIG. 2H). The lens 45 focuses the returned IR light 43 from the soil 33 into the chalcogenide fiber 47 which, in turn, transmits it up to a spectrometer 49 on the surface for analysis.

FIG. 3B shows a second configurations of the fiber optic infrared cone penetrometer. Again, the IR source 35 is down in the penetrometer tube 29. However, only one paraboloidal mirror 37 (see FIG. 2D) is used as the transmission/collection optics 23 to only direct the IR light from the source 35 through the transmission window 31 into the soil 33. Here, instead of using a second paraboloidal mirror and a focusing lens, the IR transmitting chalcogenide fiber 47 is brought up very close to the transmission window 31 to collect the IR light that is reflected from the soil 33 and transmit it to the spectrometer 49 for analysis. This second configuration of FIG. 3B has the advantage of fewer components down in the penetrometer tube 29, but it is not as efficient in collecting reflected IR light as the first configuration of FIG. 3A.

FIG. 3C shows a third configuration which is different from the configurations of FIGS. 3A and 3B. Here, the IR source 35, instead of being located in the penetrometer tube 29, is located above ground along with a beam splitter 51 and the spectrometer 49. In the operation of the third configuration of FIG. 3C, half of the light from the IR source 35 is reflected from a beam splitter 51 into the chalcogenide fiber 47 and is transmitted through the fiber 47 down from the surface into the penetrometer tube 29 before it exits the fiber 29 and impinges on an ellipsoidal mirror 53 (see FIG. 2E). The light 55 impinging on the mirror 53 is reflected out through the transmission window 31 in the penetrometer tube 29 to the soil 33. Light 55 reflected from the soil 33 through the transmission window 31 strikes the ellipsoidal mirror 53 which focuses that reflected light 55 into the fiber 47. This light is transmitted through the fiber 47 up to the surface, before exiting the fiber 47 and passing through the beam splitter 51 into the spectrometer 49 for analysis.

As discussed above, FIGS. 3A, 3B and 3C are just three examples of arranging the elements that are shown in FIGS. 2A through 2H in order to perform the operation of getting transmitted IR light to interact with the soil and then inject the reflected IR light into the IR-transmitting chalcogenide fiber for transmission to a spectrometer for wavelength and amplitude analysis.

Figure 10:
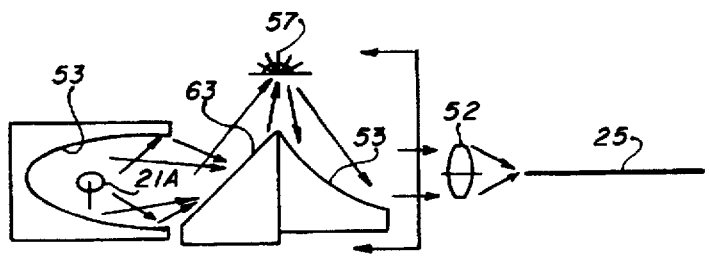
Figure 11:
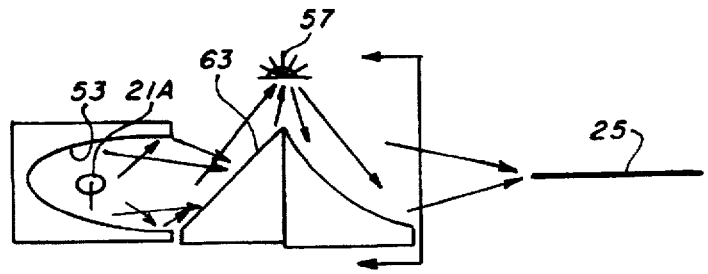
Figure 12:
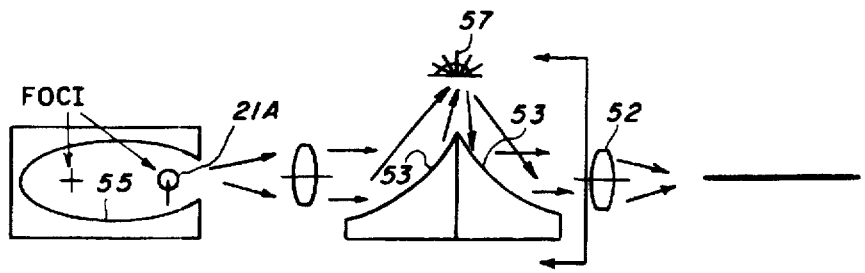

A variety of possible combinations of mirror type and source chamber geometry are shown in FIGS. 4–13. These designs all utilize a source in the penetrometer tube 29 itself such that the soil sample 33 in between the IR source 21 and the spectrometer 27. An alternative approach is to place the IR source 21 in the same remote location as the spectrometer 27 such that light is transmitted in both directions through the optical chalcogenide fiber 25: from the IR source 21 to the soil sample 33 and from the soil sample 33 to the spectrometer 27 as shown in FIG. 12. Some possible arrangements are shown in FIGS. 14–17.

Figure 4:
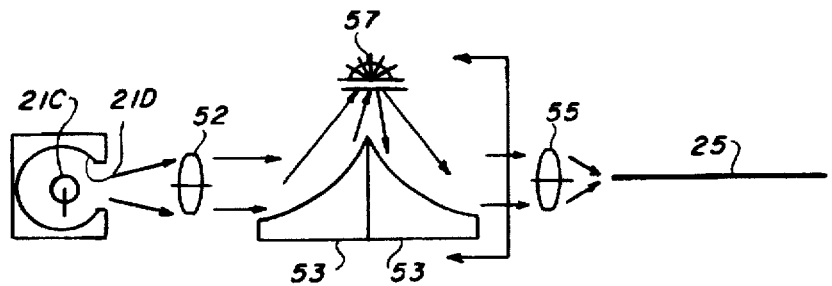
FIGS. 4 through 13 illustrate the operations of various combinations of system components between the infrared source and the infrared-transmitting chalcogenide optical fiber, where the infrared source is located within the cone penetrometer.

FIG. 4 shows an IR source 21C in a reflecting sphere 21D, a collimating lens 52, and two back-to-back paraboloidal mirrors 53, a focusing lens 55, a chalcogenide fiber 25 and the reflected light 57 from the soil 33 (FIG. 1). FIG. 4 shows a standard approach to the problem of transmitting light from the IR source 21C to a solid sample, such as soil 33 (FIG. 1), and for collecting the diffusely-reflected IR light 57 from the soil 33 in the use of the pair of off-axis paraboloidal mirrors 53. The foci of both paraboloidal mirrors 53 are coincident at a point on or just inside the surface of the sample 33 (FIG. 1). Hence, for a point source, after collimation of the beam by the lens 52, the mirror pair 53 focuses the light to the focal point and emits a collimated beam of the reflected light 57 which can be focused into the optical fiber 25 using the focusing lens 55. In practice, using a finite source, both the incident and reflected light is only partially collimated. However, sufficient optical throughput can be obtained for successful operation of the device.

Figure 5:
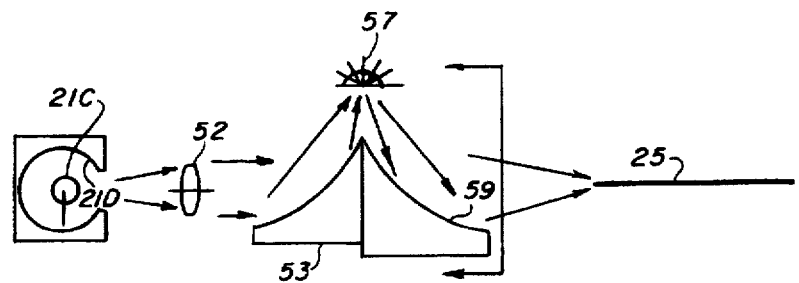

FIG. 5 shows an IR source 21C in a spherical reflecting cavity 21D, a collimination lens 52, a paraboloidal mirror 53 onto the sample 33 (FIG. 1), an ellipsoidal mirror 59 off the sample 33 and into the optical fiber 25. Here, instead of having a second paraboloidal mirror, there is an ellipsoidal mirror 59. With the use of the ellipsoidal mirror 59, which has a focusing quality, a second lens (55) is not needed. Note that the collected IR light is injected from the ellipsoidal mirror 59 right into the end of the fiber 25, which fiber 25 is located at one of the focal points discussed before) of the ellipsoidal mirror 59. Thus, any reflected light from the soil 33 that hits the ellipsoidal mirror 59 will automatically be focussed into the fiber 25.

Figure 6:
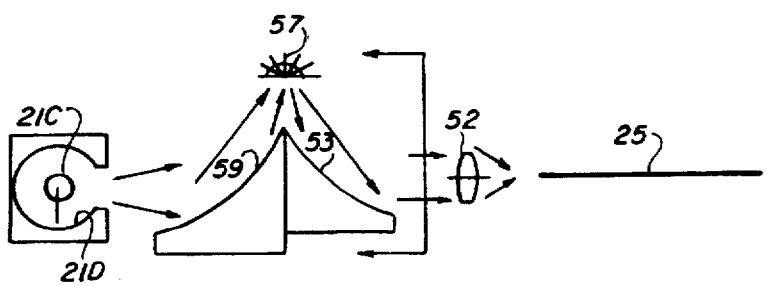

FIG. 6 shows an opposite way of performing the operation shown in FIG. 5. Here again an IR source 21C is located in a spherical reflecting cavity 21D, but an ellipsoidal mirror 59 is used to direct the IR light into the soil 33 (FIG. 1), a paraboloidal mirror 53 collects the reflected light 57 from the soil 33. However, in this case, a focusing lens 52 is needed to focus the collected reflected light into the fiber 25.

Figure 7:
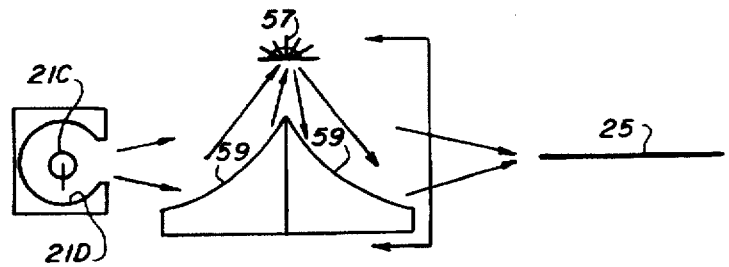

FIG. 7 shows an IR source 21C located in a spherical reflecting cavity 21D, two back-to-back ellipsoidal mirrors 59 with one ellipsoidal mirror 59 from the reflecting cavity 21D onto the soil 33 (FIG. 1) and the other ellipsoidal mirror 59 off the soil 33 and into the optical fiber 25. No lens is needed for this implementation.

Figure 8:
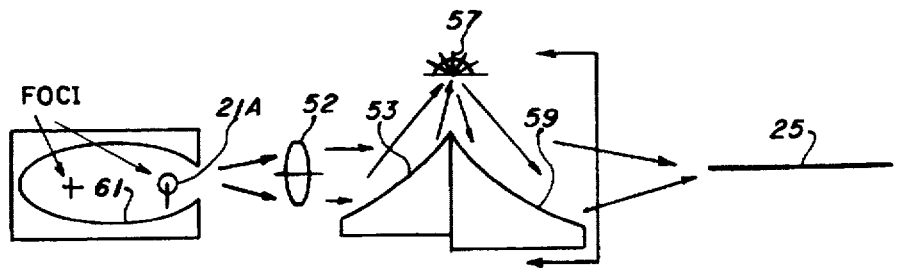

FIG. 8 uses a different type of IR source than the type shown in FIGS. 4–7. Here the IR source 21A is located at one of the focal points in a reflecting ellipsoidal cavity 61. IR light from the IR source 21A passes out of the cavity 61, is collimated by a collimating lens 52 and directed by a paraboloidal mirror 53 onto the soil 33 (FIG. 1). IR light reflected by the soil 53 is collected by an ellipsoidal mirror 59 and focused by the ellipsoidal mirror 59 into the optical fiber 25.

Figure 9:
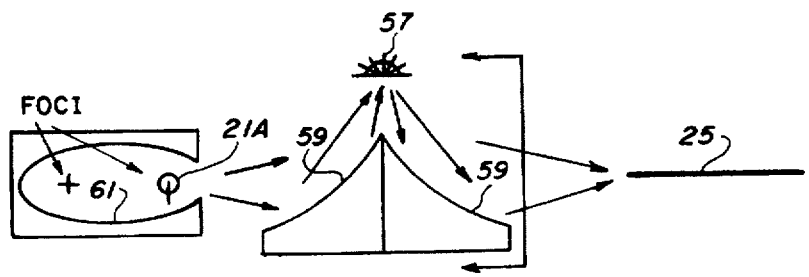

FIG. 9 shows an IR source 21A located at one of the focal points in a reflecting ellipsoidal cavity 61, two back-to-back ellipsoidal mirrors 59. IR light from the IR source 21A passes out of the cavity 61, is directed by one of the ellipsoidal mirrors 53 onto the soil 33 (FIG. 1), reflected off the soil 53, collected and focused by the second ellipsoidal mirror 59 into the optical fiber 25.

FIG. 10 shows an IR source 21A in a reflecting paraboloidal or ellipsoidal cavity 53. IR light from the cavity 53 is reflected from a flat mirror 63 onto the soil 33 (FIG. 1). IR light reflected from the soil 33 is collected by a paraboloidal mirror 53 and focused by a focusing lens 52 into the optical fiber 25.

FIG. 11 shows an IR source 21A in a reflecting paraboloidal or ellipsoidal cavity 53, a flat mirror 63 to direct IR light from the IR source 21A to the soil 33 (FIG. 1), an ellipsoidal mirror 59 to collect the reflected IR light 57 and focus it into the fiber 25.

FIG. 12 shows an ellipsoidal reflecting cavity 55 containing an IR source 21A, a lens 52 to collimate the IR light from the cavity 53, two back-to-back paraboloidal mirrors 53 with a first paraboloidal mirror 53 to direct light to the soil 33 (FIG. 1) and the second paraboloidal mirror to collect the reflected IR light 57, and a focusing lens 52 to focus the collected reflected light into the fiber 25.

Figure 13:
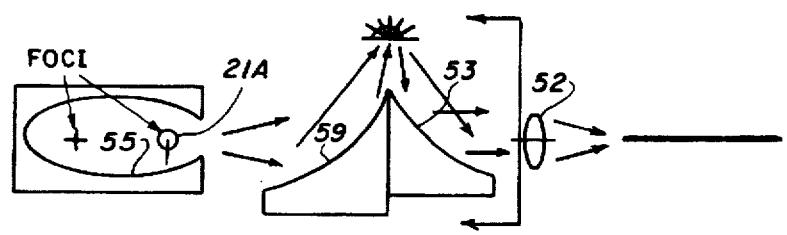

FIG. 13 shows an ellipsoidal reflecting cavity 55 containing an IR source 21A, an ellipsoidal mirror 59 used to direct the IR light from the source 21A into the soil 33 (FIG. 1), a paraboloidal mirror 53 to collect the IR light reflected from the soil 33, and a lens 52 to focus the collected IR light into the fiber 25.

FIGS. 4 through 13 have been discussed as embodiments wherein the IR source was located in the penetrometer tube 29 itself such that the soil sample 33 (FIG. 1) was between the IR source 21 and the spectrometer 27. FIGS. 14 through 17 show alternative embodiments wherein the IR source 21 is placed in the same remote location, or surface, as the spectrometer 27 such that light is transmitted in both directions through the optical chalcogenide optical fiber 25: from the IR source 21 to the soil sample 33 and from the soil sample 33 to the spectrometer 27 as shown in FIG. 12. The exemplary embodiments of FIGS. 14–17 will now be discussed.

Figure 14:
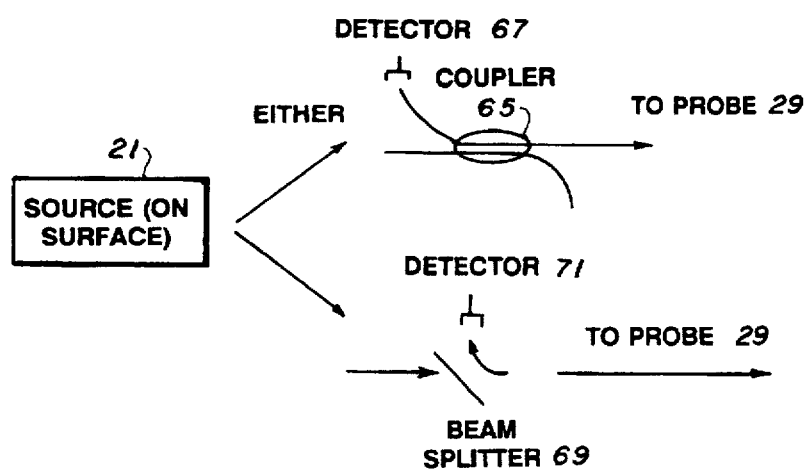
FIGS. 14 through 17 illustrate the operations of various combinations of system components, where the infrared source is located at a remote location away from the sample site, such as on the surface.

FIG. 14 shows two different techniques for placing the IR source 21 on the surface. Then the IR light from the source 21 can be coupled down into the probe or penetrometer tube 29 below ground by way of a fiber coupler 65, the transmission/collection optics 23 and the transmission window 31 and into the soil 33 (FIG. 1), and the reflected IR light returns to the fiber coupler 65 by way of the transmission window 31, the transmission/collection optics 23. The returned reflected IR light then passes through the fiber coupler 65 to a detector 57 in the spectrometer 27 (FIG. 1) for analysis. In a second technique in FIG. 14, IR light from the source 21 passes though a beam splitter or a bulk optic beam splitter 69 down to the probe 29 and also directs reflected IR light that comes back from the probe 29 to a detector 71 in the spectrometer 27 (FIG. 1) for analysis.

Figure 15:
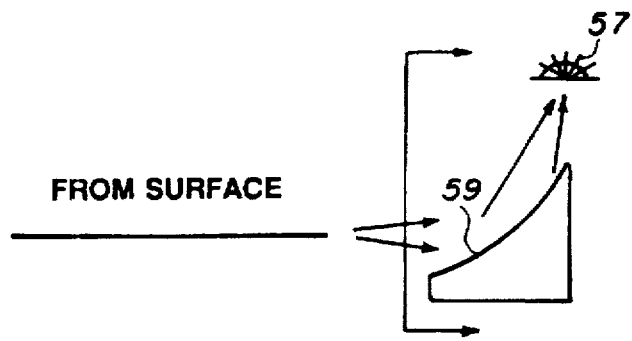

FIG. 15 shows IR light coming from (the IR source 21 on) the surface to the fiber 25, exiting the fiber 25. An ellipsoidal mirror 59 is then used to transmit the IR light out into the soil 33 (FIG. 1), recover the light reflected from the soil 33 and inject it back into the fiber 25.

Figure 16:
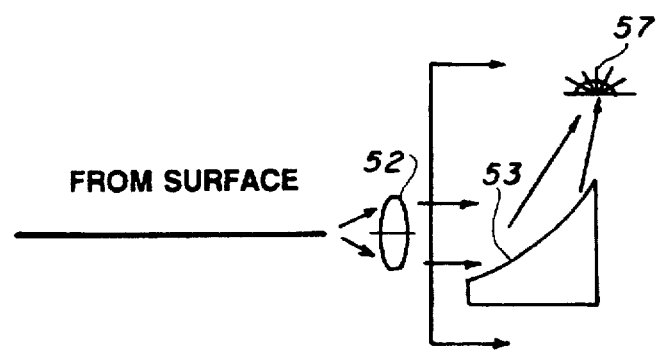

In FIG. 16, the same operation is accomplished as in FIG. 15, using the combination of a lens 52 and a paraboloidal mirror 53.

Figure 17:
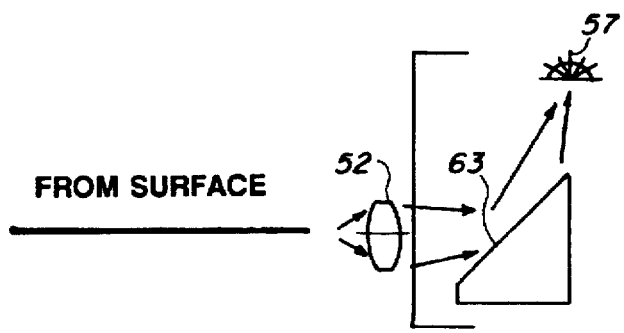

In FIG. 17, the same operation is accomplished as in FIG. 15, using the combination of a lens 52 and a flat mirror 63.

Advantages and New Features of the Invention

The essential new feature of this invention is the combination of components, including IR source, nonimaging optics, and most-importantly, IR-transmitting chalcogenide optical fiber, and optical signal processor or spectrometer to produce a system capable of remote, in-situ fiber optic IR spectroscopy in underground locations.

The advantages of the new system include: 1) the ability to perform remote, in-situ fiber optic IR spectroscopy in the wavelength range from 2 to 12 microns; 2) the ability to detect and identify chlorinated solvents in-situ, in underground locations; 3) the ability to identify the presence of individual chemicals, including water, from analysis of the IR spectrum obtained.

Alternatives

A system of the type described in this patent disclosure could be assembled using either fluoride-based optical fibers or sapphire-based optical fibers. Sapphire-based fibers are difficult to produce in lengths greater than 10–20 meters, are not mechanically robust in long lengths, and are hydroscopic, making them difficult to use in uncontrolled, outdoor environments. Fluoride-based fibers do not transmit into the infrared as far as 10 microns, are also hydroscopic and are not mechanically robust in long lengths. Polycrystalline halide fibers can be used for slightly longer wavelengths (4–15 microns) but require special handling procedures.

Therefore, what has been described in a preferred embodiment of the invention is a system for performing remote, in-situ infrared (IR) spectroscopy of soils and soil-liquid mixtures in the 2 to 12 micron wavelength range. Specifically, the invention: I) provides the means for transmitting optical radiation in the 2 to 12 micron wavelength range via a fiber optic cable to an optical system in a cone penetrometer tube; II) provides an optical system for the efficient and reproducible transmission of infrared light to a region of the soil surrounding the cone penetrometer tube; III) provides an optical system for the efficient collection of the infrared light after it has been diffusely-scattered by the soil; and IV) provides a means for efficiently coupling light from the output of the optical fiber into an optical signal processor, such as an infrared spectrometer.

The novel features of the system disclosed here in this application are the use of specially designed transmission/collection optics for transmitting infrared light out of a transmission window of a cone penetrometer tube into soil around the window and recovering some of the reflected scattered infrared light from the soil by way of the window and the transmission/collection optics, and the incorporation of optical fibers based on chalcogenide materials (S, Se, Te) which transmit infrared radiation from 2–12 microns in a ruggedized unit suitable for use in the field. This is the wavelength region where unique infrared (IR) absorption features occur for many chemical compounds. In particular, unique identification can be made of water and soil mineralogy and environmentally important contaminants such as chlorinated hydrocarbons, BTEX compounds (benzene, toluene, ethylbenzene, and xylene) and fuels.

It should therefore readily be understood that many modifications and variations of the present invention are possible within the purview of the claimed invention. It is therefore to be understood that, within the scope of the appended claims, the invention may be practiced otherwise than as specifically described.

What is claimed and desired to be secured by Letters Patent of the United States is:

1. A system for in-situ, subsurface soil measurement of chemicals, including water, in soil, said system comprising:

probe means for penetrating the soil, said probe means including interior and exterior surfaces, and a window for allowing infrared radiation within a wavelength range from about 2 microns to about 12 microns to be transmitted between said interior and exterier surfaces of said probe;

means for driving said probe means into the soil to a plurality of different depths;

means for providing infrared radiation within the wavelength range from about 2 microns to about 12 microns, which radiation passes through said window to irradiate the soil adjacent to said window;

an infrared transmitting chalcogenide optical fiber;

optical means disposed within said probe means adjacent to said window for transmitting infrared radiation within about the 2 to 12 micron wavelength range from said providing means through said window into the soil and for collecting infrared radiation within about the 2 to 12 micron wavelength range reflected from the soil back through said window into a first end of said chalcogenide optical fiber; and means coupled to a second end of said infrared transmitting chalcogenide optical fiber for receiving and analyzing the reflected infrared radiation within about the 2 to 12 micron wavelength range passing through said chalcogenide optical fiber to obtain information on chemicals present at various depths of the soil through which said probe means passes.

2. The system of claim 1 wherein:

said probe means is a cone penetrometer tube; and said providing means comprises a reflector having at least one focal point, and an infrared source located at said at least one focal point of said reflector for providing the infrared radiation.

3. The system of claim 2 wherein:

said reflector is an ellipsoidal shaped reflector.

4. The system of claim 2 wherein:

said reflector is a paraboloidal shaped reflector.

5. The system of claim 2 wherein:

said reflector is a spherical reflecting cavity.

6. The system of claim 2 wherein:

said reflector is an ellipsoidal-shaped cavity having two focal points; and said infrared source is located at one of said two focal points.

7. The system of claim 2 wherein:

said infrared source is selected from the group consisting of a nichrome wire filament, a glowbar material and an infrared laser source.

8. The system of claim 2 wherein:

said window is a sapphire window.

9. The system of claim 1 wherein:

said providing means includes an infrared source; and said optical means is an optical assembly comprised of transmission/collection optics operating over a wavelength range from about 2 microns to about 12 microns for transmitting infrared radiation from said infrared source to the soil and for collecting infrared radiation reflected by the soil.

10. The system of claim 9 wherein:

said probe means is a cone penetrometer tube that is driven into the soil by said driving means;

said infrared source and said transmission/collection optics are contained in said cone penetrometer tube; and said analyzing means is remotely located on or above the soil.

11. The system of claim 10 wherein:

said analyzing means is a spectrometer.

12. The system of claim 10 wherein:

said infrared source transmits infrared radiation through said transmission/collection optics and through said window into the soil adjacent to said window;

said transmission/collection optics collects infrared radiation reflected from the soil through said window and injects said reflected infrared radiation into said infrared transmitting chalcogenide optical fiber;

said infrared transmitting chalcogenide optical fiber transmits said reflected infrared radiation from said cone penetrometer tube to said analyzing means; and said analyzing means analyzes said reflected infrared radiation from said chalcogenide optical fiber to obtain information on chemicals present at various depths of the soil through which said cone penetrometer tube passes.

13. The system of claim 12 wherein:

said transmission/collection optics comprises a paraboloidal mirror to direct the infrared radiation from said infrared source through said window into the soil; and said chalcogenide optical fiber has a first end positioned close to said window to collect the infrared radiation reflected from the soil and through said window and a second end coupled to said analyzing means for transmitting the reflected radiation to said analyzing means for analysis.

14. The system of claim 9 further including a mirror disposed in said probe means and a beamsplitter and wherein:

said probe means is a cone penetrometer tube that is driven into the soil by said driving means;

said transmission/collection optics is contained in said cone penetrometer tube;

said analyzing means is remotely located at or above the soil;

said beam splitter is remotely located on or above the soil between said analyzing means and said chalcogenide optical fiber;

said infrared source is remotely located on or above the soil for transmitting infrared radiation to said beam splitter;

said beam splitter reflecting infrared radiation into said chalcogenide fiber and into said cone penetrometer tube;

said mirror reflecting said infrared radiation from said chalcogenide fiber through said window of said cone penetrometer tube to the soil, said mirror focusing infrared radiation reflected from the soil into said chalcogenide fiber for transmission of said focused reflected infrared radiation through said beamsplitter and into said analyzing means for analysis.

15. The system of claim 14 wherein:

said mirror is an ellipsoidal mirror.

16. The system of claim 9 further including a mirror disposed in said probe means and a fiber coupler and wherein:

said probe means is a cone penetrometer tube that is driven into the soil by said driving means;

said transmission/collection optics is contained in said cone penetrometer tube;

said analyzing means is remotely located at or above the soil;

said fiber coupler is remotely located on or above the soil between said analyzing means and said chalcogenide optical fiber;

said infrared source is remotely located on or above the soil for transmitting infrared radiation to said fiber coupler;

said fiber coupler passing infrared radiation through said chalcogenide fiber and into said cone penetrometer tube;

said mirror reflecting said infrared radiation from said chalcogenide fiber through said window of said cone penetrometer tube to the soil, said mirror focusing infrared radiation reflected from the soil into said chalcogenide fiber for transmission of said focused reflected infrared radiation through said fiber coupler and into said analyzing means for analysis.

17. The system of claim 16 wherein:

said mirror is an ellipsoidal mirror.

18. The system of claim 1 wherein:

said analyzing means is a spectrometer.

19. The system of claim 18 wherein:

said spectrometer is an infrared spectrometer.

20. The system of claim 18 wherein:

said spectrometer is a Fourier transform infrared spectrometer.

21. The system of claim 18 wherein said spectrometer comprises:

a dispersive spectrometer selected from the group consisting of a monochromator, a polychrometer, a scanning monochromator and a spectrograph.

22. The system of claim 1 wherein:

said providing means includes an infrared source for producing a wideband wavelength range within a wavelength range from about 2 microns to about 12 microns.

23. The system of claim 1 wherein:

said providing means includes an infrared source for producing a narrowband wavelength range within a wavelength range of from about 2 microns to about 12 microns.

24. The system of claim 1 wherein:

said infrared transmitting chalcogenide optical fiber has an attenuation of not more than 1 dB per meter within the wavelength range from about 2 microns to about 12 microns.

25. The system of claim 24 wherein:

said infrared transmitting chalcogenide optical fiber is based on chalocogenide materials selected from the group of chemical compositions consisting of $As_2S_3$, $As_2Se_3$ and $As_2Te_3$.

26. A system for in-situ, subsurface soil measurement of chemicals, including water, in soil, said system comprising:

probe means for penetrating the soil, said probe means including interior and exterior surfaces, and a window for allowing infrared radiation to be transmitted between said interior and exterior surfaces of said probe, said probe means is a cone penetrometer tube that is driven into the soil by said driving means;

means for driving said probe means into the soil to a plurality of different depths;

means for providing infrared radiation which passes through said window to irradiate the soil adjacent to said window, said providing means including an infrared source;

an infrared transmitting chalcogenide optical fiber;

said transmission/collection optics comprises first and second back-to-back paraboloidal mirrors, said first paraboloidal mirror reflecting the infrared radiation from said infrared source through said window into the soil, said second paraboloidal mirror directing infrared radiation reflected from the soil and through said window to said focusing lens; and said focusing lens focusing the reflected infrared radiation into said chalcogenide optical fiber;

optical means disposed within said probe means adjacent to said window for transmitting infrared radiation from said providing means through said window into the soil and for collecting infrared radiation reflected from the soil back through said window into a first end of said chalcogenide optical fiber, said optical means is an optical assembly comprised of transmission/collection optics operating over a wavelength range from about 2 microns to about 12 microns for transmitting infrared radiation from said infrared source through said transmission/collection optics and through said window into the soil adjacent to said window and for collecting infrared radiation reflected from the soil through said window and for injecting said reflected infrared radiation into said transmitting chalcogenide optical fiber, said infrared transmitting chalcogenide optical fiber transmitting said reflected infrared radiation from said cone penetrometer tube to said analyzing means, said infrared source and said transmission/collection optics are contained in said cone penetrometer tube;

means coupled to a second end of said infrared transmitting chalcogenide optical fiber for analyzing the reflected infrared radiation passing through said chalcogenide optical fiber to obtain information on chemicals present at various depths of the soil through which said probe means passes, said analyzing means being remotely located on or above the soil, said analyzing means analyzing said reflected infrared radiation from said chalcogenide optical fiber to obtain information on chemicals present at various depths of the soil through which said cone penetrometer tube passes;

said infrared source transmits infrared radiation through said transmission/collection optics and through said window into the soil adjacent to said window;

said transmission/collection optics collects infrared radiation reflected from the soil through said window and injects said reflected infrared radiation into said infrared transmitting chalcogenide optical fiber;

said infrared transmitting chalcogenide optical fiber transmits said reflected infrared radiation from said cone penetrometer tube to said remotely located processing means; and said analyzing means analyzes said reflected infrared radiation from said chalcogenide optical fiber to obtain information on chemicals present at various depths of the soil through which said cone penetrometer tube passes.

27. The system of claim 26 further including:

a collimating lens disposed between said infrared source and said first paraboloidal mirror for collimating the infrared radiation from said infrared source, said first paraboloidal mirror focusing the collimated infrared radiation to a focal point in the soil.

* * * * *